United States Patent
Kim et al.

(10) Patent No.: US 10,088,376 B2
(45) Date of Patent: Oct. 2, 2018

(54) CONTACT PRESSURE MEASURING APPARATUS, METHOD OF MANUFACTURING THE SAME AND METHOD OF MEASURING CONTACT PRESSURE

(71) Applicant: SAMSUNG ELECTRONICS CO., LTD., Suwon-si (KR)

(72) Inventors: Sangkyu Kim, Yongin-si (KR); Joonhyung Lee, Yongin-si (KR); Seongho Cho, Gwacheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 242 days.

(21) Appl. No.: 14/820,653

(22) Filed: Aug. 7, 2015

(65) Prior Publication Data

US 2016/0069756 A1  Mar. 10, 2016

(30) Foreign Application Priority Data

Sep. 5, 2014 (KR) .......................... 10-2014-0119371

(51) Int. Cl.
*G01L 1/24* (2006.01)
*G01N 21/17* (2006.01)
(Continued)

(52) U.S. Cl.
CPC .............. *G01L 1/24* (2013.01); *G06F 3/0414* (2013.01); *G06F 3/0421* (2013.01); *G01L 1/241* (2013.01); *G01L 1/25* (2013.01); *G01L 9/0076* (2013.01); *G01L 11/02* (2013.01); *G01N 23/046* (2013.01); *G01N 2021/1787* (2013.01);
(Continued)

(58) Field of Classification Search
CPC ... G01L 1/24; G01L 1/241; G01L 1/25; G01L 11/02; G01L 9/0076; G01N 2021/1787; G01N 21/552; G01N 2223/419; G01N 23/046; G01F 2203/04104; G01F 2203/04109; G06F 3/0325; G06F 3/041; G06F 3/042; G06F 3/0421; G06F 3/0423; G06F 3/0428; H01L 2224/04;
(Continued)

(56) References Cited

U.S. PATENT DOCUMENTS 4,120,585 A * 10/1978 DePalma ........... G06K 9/00046
356/71
4,254,333 A * 3/1981 Bergstrom ............... G01V 8/14
250/221

(Continued)

FOREIGN PATENT DOCUMENTS

JP 2004-163311 A 6/2004
JP 2006-194800 A 7/2006

*Primary Examiner* — Jonathan Dunlap
(74) *Attorney, Agent, or Firm* — Sughrue Mion, PLLC

(57) ABSTRACT

An apparatus and method for measuring a contact pressure and a method of manufacturing the apparatus. The apparatus includes: a material layer configured to provide a light path along which incident light travels to a subject being in contact with the material layer; a spectrum analyzer configured to detect light emitted from the material layer and perform a light absorption spectrum analysis on the detected light to determine an intensity of the detected light; and a pressure calculator configured to determine the contact pressure of the subject based on the determined intensity.

17 Claims, 4 Drawing Sheets

(51) Int. Cl.

| | |
|---|---|
| G01L 9/00 | (2006.01) |
| G06F 3/041 | (2006.01) |
| G06F 3/042 | (2006.01) |
| G01L 11/02 | (2006.01) |
| G01N 23/046 | (2018.01) |
| G06F 3/03 | (2006.01) |
| G01L 1/25 | (2006.01) |

(52) U.S. Cl.
CPC ...... *G01N 2223/419* (2013.01); *G06F 3/0325* (2013.01); *G06F 3/041* (2013.01); *G06F 3/042* (2013.01); *G06F 3/0423* (2013.01); *G06F 3/0428* (2013.01); *G06F 2203/04104* (2013.01); *G06F 2203/04109* (2013.01)

(58) Field of Classification Search
CPC ....... H01L 2224/04042; H01L 2224/81; H01L 2224/97; H01L 24/97; H01L 2924/181
USPC .......... 345/173, 175; 356/136, 300, 32, 326, 356/432, 445, 485; 385/12, 13, 36; 600/300, 310; 73/800, 818, 862.046, 73/862.624
See application file for complete search history.

(56) References Cited

U.S. PATENT DOCUMENTS

| | | | |
|---|---|---|---|
| 5,004,913 A | 4/1991 | Kleinerman | |
| 5,596,320 A * | 1/1997 | Barnes | B64D 15/20 250/574 |
| 5,619,586 A * | 4/1997 | Sibbald | G06K 9/00046 356/71 |
| 6,424,851 B1 | 7/2002 | Berman et al. | |
| 6,912,912 B2 | 7/2005 | Reichinger et al. | |
| 7,697,141 B2 * | 4/2010 | Jones | E21B 47/102 356/445 |
| 7,705,835 B2 * | 4/2010 | Eikman | G06F 3/0425 178/18.01 |
| 7,991,257 B1 * | 8/2011 | Coleman | B29D 11/0073 264/1.24 |
| 7,995,039 B2 * | 8/2011 | Eliasson | G06F 3/0421 178/18.09 |
| 8,144,271 B2 * | 3/2012 | Han | G06F 3/0425 345/175 |
| 8,248,588 B2 * | 8/2012 | Azimi | G01J 3/02 356/301 |
| 8,249,408 B2 * | 8/2012 | Coleman | B29D 11/0073 156/219 |
| 8,259,240 B2 * | 9/2012 | Han | G06F 3/0425 345/175 |
| 8,441,467 B2 * | 5/2013 | Han | G06F 3/04883 178/18.09 |
| 8,525,995 B2 * | 9/2013 | Jones | E21B 47/102 356/402 |
| 8,553,014 B2 * | 10/2013 | Holmgren | G06F 3/0421 345/173 |
| 8,736,581 B2 * | 5/2014 | Han | G06F 3/0412 178/18.09 |
| 8,803,848 B2 * | 8/2014 | Suarez Rovere | G06F 3/0421 345/176 |
| 8,847,925 B2 * | 9/2014 | Ronka | G02B 6/0021 178/18.01 |
| 8,896,575 B2 * | 11/2014 | Goertz | G06F 3/042 178/18.09 |
| 8,947,666 B2 * | 2/2015 | Jones | E21B 47/102 356/402 |
| 9,134,842 B2 * | 9/2015 | Li | G06F 3/0421 |
| 9,405,382 B2 * | 8/2016 | Drumm | G06F 3/0308 |
| 9,554,738 B1 * | 1/2017 | Gulati | A61B 5/1455 |
| 2003/0176775 A1 * | 9/2003 | Berman | A61B 5/14532 600/310 |
| 2008/0007541 A1 * | 1/2008 | Eliasson | G06F 3/0421 345/176 |
| 2008/0007542 A1 * | 1/2008 | Eliasson | G06F 3/0346 345/176 |
| 2010/0001962 A1 * | 1/2010 | Doray | G06F 3/0317 345/173 |
| 2010/0123678 A1 * | 5/2010 | Kim | G06F 3/044 345/174 |
| 2010/0167451 A1 * | 7/2010 | Derderian | H01L 23/3128 438/64 |
| 2011/0074736 A1 * | 3/2011 | Takakura | G06F 3/03547 345/175 |
| 2012/0068971 A1 * | 3/2012 | Pemberton-Pigott | G06F 3/016 345/175 |
| 2012/0162142 A1 * | 6/2012 | Christiansson | G06F 3/0421 345/175 |
| 2012/0169672 A1 * | 7/2012 | Christiansson | G06F 3/0421 345/175 |
| 2012/0170056 A1 * | 7/2012 | Jakobsen | G02B 5/045 356/614 |
| 2012/0182265 A1 * | 7/2012 | Smith | G06F 3/042 345/175 |
| 2012/0188188 A1 * | 7/2012 | Smith | G06F 3/0412 345/173 |
| 2012/0200538 A1 * | 8/2012 | Christiansson | G06F 3/0418 345/175 |
| 2012/0201716 A1 * | 8/2012 | Matsuo | G01N 21/553 422/69 |
| 2012/0256882 A1 * | 10/2012 | Christiansson | G06F 3/0418 345/175 |
| 2012/0306815 A1 * | 12/2012 | Su | G06F 3/042 345/175 |
| 2013/0141364 A1 * | 6/2013 | Lynn | G06F 3/041 345/173 |
| 2013/0187891 A1 * | 7/2013 | Eriksson | G06F 3/0421 345/175 |
| 2013/0222785 A1 * | 8/2013 | Sasaki | G01C 3/08 356/4.09 |
| 2013/0285977 A1 * | 10/2013 | Baharav | G06F 3/0414 345/174 |
| 2014/0071094 A1 * | 3/2014 | Holmgren | G06F 3/0421 345/175 |
| 2014/0085241 A1 * | 3/2014 | Christiansson | G06F 3/0418 345/173 |
| 2014/0098058 A1 * | 4/2014 | Baharav | G06F 3/0421 345/174 |
| 2014/0363293 A1 * | 12/2014 | Kim | F03D 11/0025 416/5 |
| 2015/0177142 A1 * | 6/2015 | Hoult | G01J 3/28 356/326 |
| 2015/0265190 A1 * | 9/2015 | Ikebe | A61B 5/021 600/316 |
| 2015/0323385 A1 * | 11/2015 | Han | G01J 3/36 356/300 |
| 2015/0331546 A1 * | 11/2015 | Craven-Bartle | G02B 5/00 345/175 |
| 2016/0026250 A1 * | 1/2016 | Eriksson | G06F 3/0421 345/175 |
| 2016/0045143 A1 * | 2/2016 | Lee | A61B 5/1455 600/322 |
| 2016/0051175 A1 * | 2/2016 | Lee | A61B 5/165 600/310 |
| 2016/0058381 A1 * | 3/2016 | Lee | A61B 5/6843 600/547 |
| 2016/0084973 A1 * | 3/2016 | Gibson | G01T 1/24 378/62 |
| 2016/0089088 A1 * | 3/2016 | Kim | A61B 5/7278 600/473 |

\* cited by examiner

CONTACT PRESSURE MEASURING APPARATUS, METHOD OF MANUFACTURING THE SAME AND METHOD OF MEASURING CONTACT PRESSURE

CROSS-REFERENCE TO RELATED APPLICATION

This application claims priority from Korean Patent Application No. 10-2014-0119371, filed on Sep. 5, 2014 in the Korean Intellectual Property Office, the disclosure of which is incorporated herein in its entirety by reference.

BACKGROUND

1. Field

Apparatuses and methods consistent with exemplary embodiments relate to obtaining data generated by contacting a subject, and more particularly to, a contact pressure measuring apparatus, a method of measuring contact pressure using the apparatus and a method of manufacturing the apparatus.

2. Description of the Related Art

Various types of data regarding a subject may be obtained when diagnosing the subject. However, when the subject is a living body, the subject may move during a diagnosis process, and thus desired information regarding the subject may be affected due movement of the subject when diagnosis is performed.

Accordingly, the reliability of information obtained through diagnosis may be increased by correcting the information or by using a correction system embedded in a diagnosis device during the diagnosis.

An example of information obtained through a subject diagnosis process may be subject contact pressure. The accuracy of measured data may be increased by consistently maintaining the subject contact pressure. The subject contact pressure may be currently measured in a mechanical way.

SUMMARY

One or more exemplary embodiments provide an apparatus for measuring contact pressure in an optical way.

Further, one or more exemplary embodiments provide a method of manufacturing apparatuses for measuring contact pressure in an optical way.

Further still, one or more exemplary embodiments provide a method of measuring contact pressure using the apparatuses for measuring contact pressure in an optical way According to an aspect of an exemplary embodiment, there is provided an apparatus for measuring contact pressure, the apparatus including: a material layer configured to provide a light path along which incident light travels to a subject being in contact with the material layer; a spectrum analyzer configured to detect light emitted from the material layer and perform a light absorption spectrum analysis on the detected light to determine an intensity of the detected light; and a pressure calculator configured to determine the contact pressure of the subject based on the determined intensity.

The spectrum analyzer and the pressure calculator may be mounted on a same substrate.

The pressure calculator may be separately independently provided from the material layer and the spectrum layer. The apparatus may further include a substrate on which the spectrum analyzer is mounted, and the pressure calculator is provided outside the substrate, the pressure calculator is electrically connected to the spectrum analyzer through the substrate. The apparatus may further include a substrate on which the spectrum analyzer is mounted, a contact pad formed on the substrate, wherein the pressure calculator is electrically connected to the spectrum analyzer through the contact pad.

The spectrum analyzer may include light absorption spectrum data measured at various contact pressures.

The pressure calculator may include mapping data indicating relation between a plurality of contact pressure values and a corresponding plurality of light intensity values.

The material layer may be an attenuated total reflectance (ATR) crystalline layer.

The apparatus may further include a light source configured to emit the incident light to the material layer with an incidence angle and adjust the incidence angle to be greater than a critical angle to occur total internal reflection.

The spectrum analyzer may be further configured to perform the light absorption spectrum analysis based on a wavelength or a range of wavelengths of the detected light, and the pressure calculator may be further configured to consider the wavelength or the range of wavelengths of the detected light to determine the contact pressure.

According to an aspect of another exemplary embodiment, there is provided a method of manufacturing a contact pressure measuring apparatus, the method including: providing a light source and a spectrum analyzer on a substrate; forming, on the substrate, a structure that covers the light source and the spectrum analyzer; forming a material layer which is disposed on a surface of the structure and has a total reflection characteristic; and providing a pressure calculator connected to the spectrum analyzer.

The pressure calculator may be provided on the substrate.

The pressure calculator may be provided outside the substrate.

The structure may be a housing or a material layer. When the structure is the housing, the surface of the structure may correspond to a ceiling of the housing and the structure is mounted on the substrate to cover the light source and the spectrum analyzer.

The method may further include: when the structure is the material layer, forming a groove to mount the material layer thereon; and attaching the material onto the groove.

According to an aspect of another exemplary embodiment, there is provided a method of a contract pressure measuring apparatus, the method including: detecting a light absorption spectrum with respect to a subject; analyzing the detected light absorption spectrum; obtaining light intensity data that corresponds to a result of the analyzing; and outputting a pressure value corresponding to the obtained light intensity data.

The detecting the light absorption spectrum may include: recognizing that a material layer of the apparatus is in contact with the subject; radiating light into the material layer; and detecting light emitted through a light emission surface of the material layer.

The method may further include: displaying the output pressure value on a display.

BRIEF DESCRIPTION OF THE DRAWINGS

The above and/or other aspects will become apparent and more readily appreciated from the following description of the embodiments, taken in conjunction with the accompanying drawings in which.

DETAILED DESCRIPTION

Figure 1:
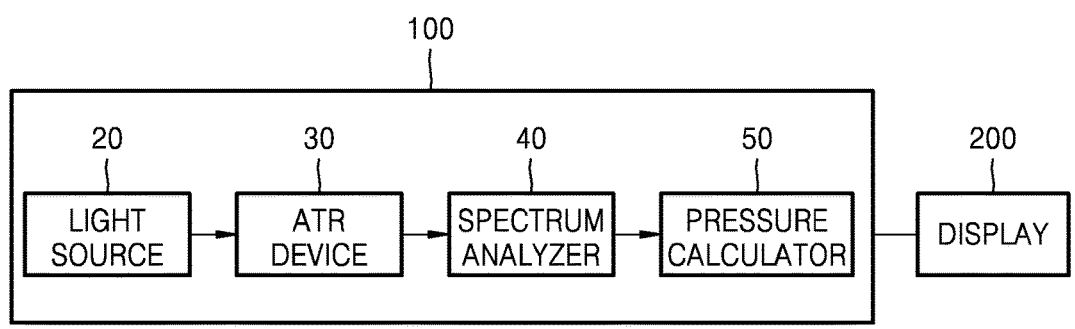
FIG. 1 is a block diagram of a subject contact pressure measuring apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

An subject contact pressure measuring apparatus using optical absorptivity of subject (hereinafter, a pressure measuring apparatus) according to an exemplary embodiment will be described as well as a method of manufacturing the pressure measuring apparatus and a method of measuring subject contact pressure using the pressure measuring apparatus.

First, a pressure measuring apparatus according to an embodiment is described.

FIG. 1 is a block diagram of a pressure measuring apparatus 100 according to an exemplary embodiment.

As shown in FIG. 1, the pressure measuring apparatus 100 includes a light source 20, an attenuated total reflectance (ATR) device 30 including a total reflection material layer, a spectrum analyzer 40, and a pressure calculator 50. The light source 20 radiates light onto the ATR device 30. The light source 20 may be, for example, a laser light source, a light-emitting diode (LED), etc. The laser light source may be a semiconductor laser. The light radiated onto the ATR device 30 from the light source 20 may be transferred to the spectrum analyzer 40 through internal total reflection. Specifically, the ATR device 30 may include a crystal of a high refractive index, and light incident on the ATR device 30 may undergo multiple internal reflections in the crystal and be collected by the spectrum analyzer 40 as it exits the crystal. When a subject is in contact with the ATR device 30 during the internal total reflections, a part of the light is absorbed by the subject and the remaining light is transferred to the spectrum analyzer 40. That is, a light absorption spectrum of the subject is transferred to the spectrum analyzer 40. A spectrum of the light transferred to the spectrum analyzer 40 may be analyzed so that data of the spectrum intensity (for example, the intensity of light having a wavelength) of the transferred light may be output. The spectrum of the transferred light may be analyzed by using a specific wavelength or a range of wavelengths that belongs to a spectrum range. For example, the intensity of light corresponding to the specific wavelength or the range of wavelengths may be analyzed from the spectrum of the transferred light and data of the intensity of the light having the specific wavelength or the range of wavelengths may be output. The specific wavelength or the range of wavelengths may correspond to a wavelength having no an optical reaction (for example, light absorption) or having a minimum optical reaction with structure (or chemical) constituting the subject.

The output data is transferred to the pressure calculator 50. The pressure calculator may be implemented by a processor and a memory. The pressure calculator 50 calculates pressure from the data transferred from the spectrum analyzer 40 based on a predetermined algorithm. The calculated pressure is subject contact pressure with respect to the pressure measuring apparatus 100 (or the ATR device 30). Data of the light absorption spectrum of the subject measured at various contact pressures may be stored in the spectrum analyzer 40 during a process of manufacturing the pressure measuring apparatus 100. The spectrum analyzer 40 may compare and analyze the light absorption spectrum transferred from the ATR device 30 by using the stored data as a database to obtain data regarding the intensity of the light absorption spectrum at a specific location.

The pressure calculator 50 may store data of the intensity of the light absorption spectrum—the contact pressure based on data regarding the intensity of the light absorption spectrum of the subject that is measured at various contact pressures and data regarding the various contact pressures during the process of manufacturing the pressure measuring apparatus 100. Specifically, the pressure calculator 50 may use mapping data indicating relation between a plurality of contact pressure values and a corresponding plurality of light intensity values. Thus, if the intensity of a predetermined location of the light absorption spectrum of the subject is provided to the pressure measuring apparatus 100, the subject contact pressure may be output. The pressure measuring apparatus 100 may include a display window to display the output subject contact window. Alternatively, the pressure measuring apparatus 100 may transfer data regarding the output subject contact pressure to a display 200 that is spaced apart therefrom to display the output subject contact pressure on the display 200.

Figure 2:
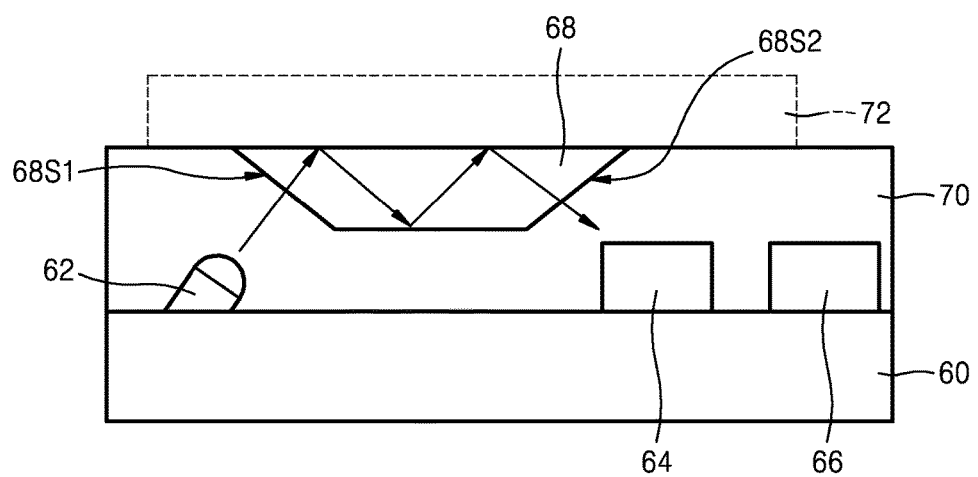
FIG. 2 is a detailed diagram of the subject contact pressure measuring apparatus of FIG. 1 according to an exemplary embodiment.

FIG. 2 is a detailed diagram of the pressure measuring apparatus 100 of FIG. 1.

As shown in FIG. 2, a light source 62, a spectrum analyzer 64, and a pressure calculator 66 are provided on a substrate 60. The substrate 60 may be, for example, a printed circuit board. The spectrum analyzer 64 may be provided at a location facing a light emission surface 68S2 of an ATR crystalline layer 68. The spectrum analyzer 64 may detect and analyze light emitted from the light emission surface 68S2 of the ATR crystalline layer 68. The spectrum analyzer 64 and the pressure calculator 66 are spatially spaced apart from each other but are electrically connected to each other. That is, the spectrum analyzer 64 and the pressure calculator 66 may be connected to each other by an electric wiring for data transfer. The light source 62 may be, for example, a laser diode (LD), an LED, etc. but is not limited thereto. An incident angle of light incident onto a light incident surface 68S1 of the ATR crystalline layer 68 from the light source 62 may be an angle at which the light incident onto the ATR crystalline layer 68 makes total reflection in upper and lower surfaces of the ATR crystalline layer 68. For example, if the incident angle of the light is adjusted to be greater than a critical angle, the light does not cross the boundaries of the ATR crystalline layer 68 and be totally reflected back internally. Here, the critical angle refers to an angle above which total internal reflection occurs.

When a subject 72 contacts the upper surface of the ATR crystalline layer 68, a total reflection condition for the upper surface of the ATR crystalline layer 68 may differ than when the subject 72 is not in contact with the ATR crystalline layer 68. For example, a part of the light incident onto the upper surface of the ATR crystalline layer 68 is absorbed by the subject 72, and the remaining light is reflected into the ATR crystalline layer 68. The light reflected into the ATR crystalline layer 68 is totally reflected from the lower surface of the ATR crystalline layer 68. The light incident in the ATR crystalline layer 68 transmits the ATR crystalline layer 68 in the manner described above and is emitted through the light emission surface 68S2. The light emitted through the light emission surface 68S2 of the ATR crystalline layer 68 includes light absorption information regarding a plurality of regions of the subject 72. Thus, the spectrum analyzer 64 may detect the light emitted through the light emission surface 68S2 of the ATR crystalline layer 68 and extract light intensity data regarding a specific location of an absorption spectrum of the detected light through spectrum analysis. The extracted light intensity data is transferred to the pressure calculator 66 via the electric wiring. The pressure calculator 66 analyzes the light intensity data transferred from the spectrum analyzer 64 and outputs contact pressure corresponding to the light intensity data.

A structure 70 may cover the light source 62, the spectrum analyzer 64, and the pressure calculator 66. When the structure 70 is a housing (or a case), the ATR crystalline layer 68 may be attached to a ceiling of the structure 70. A part of the structure 70 contacting the ATR crystalline layer 68 may be transparent.

According to another example, the structure 70 is not the housing and may be a material layer covering the light source 62, the spectrum analyzer 64, and the pressure calculator 66 and may include a groove for mounting the ATR crystalline layer 68. In this case, a refractive index of the structure 70 may be smaller than that of the ATR crystalline layer 68 that may be mounted in the groove. The ATR crystalline layer 68 may be an example of a material layer exhibiting an ATR characteristic.

Figure 3:
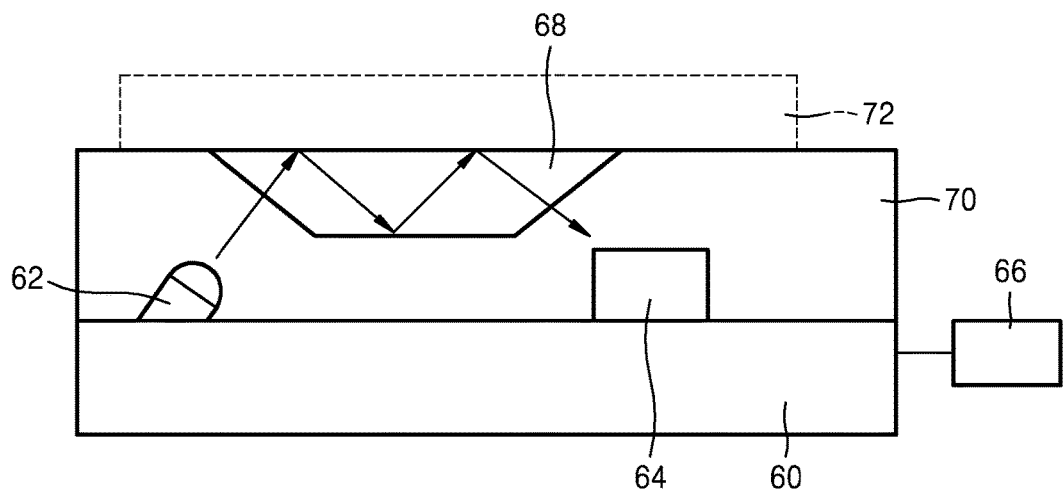
FIG. 3 is a cross-sectional view of a subject pressure measuring apparatus including a pressure calculator of FIG. 2 that is connected to a substrate and independently separate from other elements, according to an exemplary embodiment.
Figure 4:
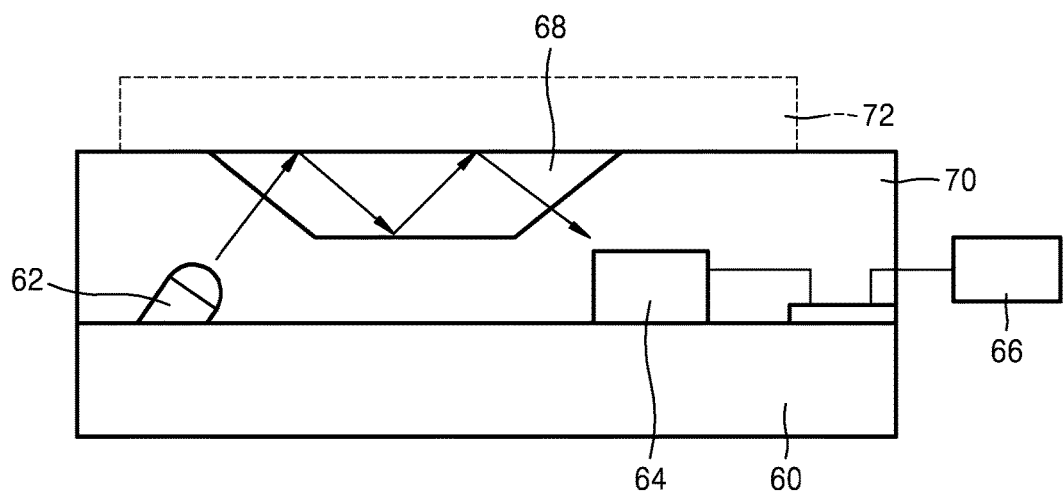
FIG. 4 is a cross-sectional view of a pressure measuring apparatus including a pressure calculator of FIG. 2 that is connected to a spectrum analyzer through a contact pad and independently separate from other elements, according to an exemplary embodiment.

The pressure calculator 66 may be separate from other elements including the substrate 60 and may be independently provided as the examples illustrated in FIGS. 3 and 4.

As shown in FIG. 3, the pressure calculator 66 is present outside the substrate 60 and the structure 70. The pressure calculator 66 may be electrically connected to the substrate 60. Thus, the pressure calculator 66 may be electrically connected to the spectrum analyzer 64 through the substrate 60.

As shown in FIG. 4, the pressure calculator 66 disposed outside the substrate 60 and the structure 70 may be electrically connected to the spectrum analyzer 64 through a contact pad 80 provided on the substrate 60. The contact pad 80 is spatially spaced apart from the spectrum analyzer 64 but is electrically connected thereto. The pressure calculator 66 of FIGS. 3 and 4 may be provided with a display apparatus on which contact pressure output by the pressure calculator 66 is displayed.

A method of manufacturing a pressure measuring apparatus, according to an embodiment, will now be described with reference to FIGS. 5 through 7. The same reference numerals denote the same elements throughout.

Figure 5:
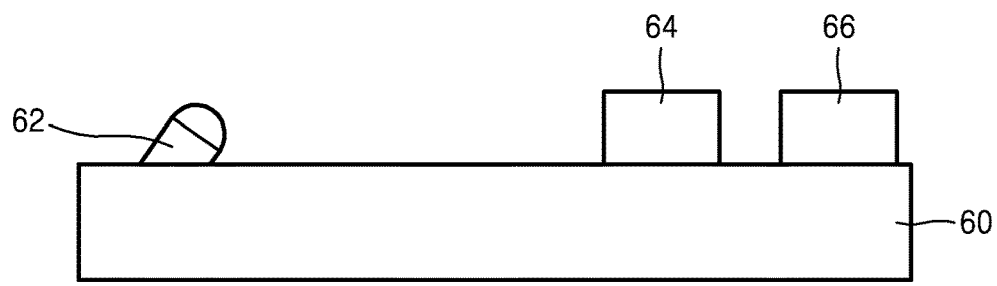
FIGS. 5 through 7 are cross-sectional views of a subject contact pressure measuring apparatus for explaining a method of manufacturing the subject contact pressure measuring apparatus according to an exemplary embodiment.

As shown in FIG. 5, the light source 62, the spectrum analyzer 64, and the pressure calculator 66 are mounted on the substrate 60. The light source 62 and the spectrum analyzer 64 may be disposed in consideration of locations of light incident and emission surfaces of the ATR crystalline layer 68. The pressure calculator 66 may not be mounted on the substrate 60 but may be separately provided outside the substrate 60 (see FIGS. 3 and 4).

Figure 6:
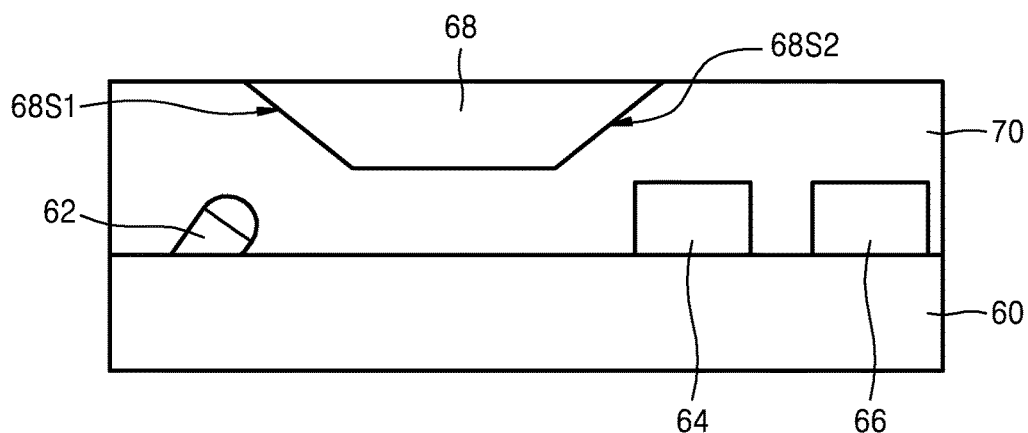
Figure 7:
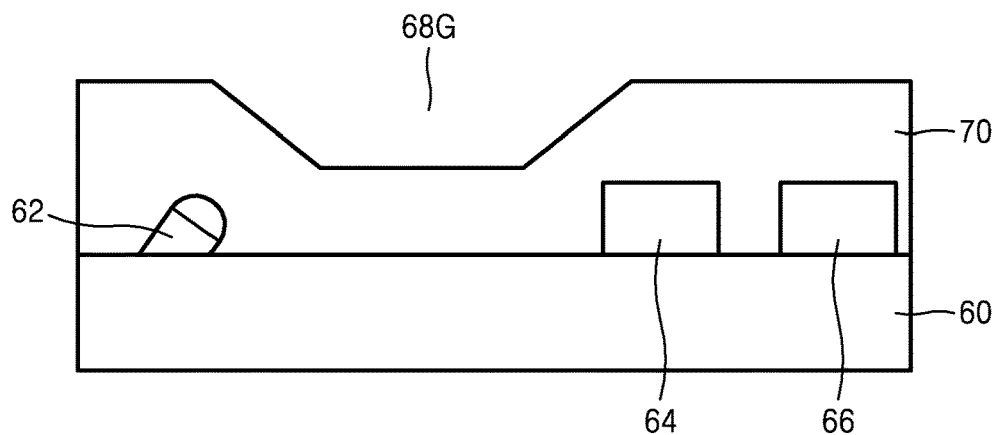

As shown in FIG. 6, the structure 70 that covers the light source 62, the spectrum analyzer 64, and the pressure calculator 66 are formed on the substrate 60. When the structure 70 is a housing, the ATR crystalline layer 68 is attached to a ceiling of the structure 70 before the structure 70 is mounted on the substrate 60. Thereafter, the structure 70 may be mounted in such a way that the ATR crystalline layer 68 is disposed between the light source 62 and the spectrum analyzer 64. When the structure 70 is a material layer having a refractive index that is smaller than that of the structure 70, as shown in FIG. 7, the structure 70 that covers the light source 62, the spectrum analyzer 64, and the pressure calculator 66 is formed on the substrate 60, and then a groove 68G for attaching the ATR crystalline layer 68 is formed in a location on which the ATR crystalline layer 68 of the structure 70 is to be attached. In this regard, one side of an inclination surface of the groove 68G is parallel to the light incident surface of the ATR crystalline layer 68, and the other side thereof is parallel to the light emission surface of the ATR crystalline layer 68. After the groove 68G is formed, the ATR crystalline layer 68 is attached into the groove 68G of the structure 70. In this regard, an adhesive agent that does not prevent light from being incident and emitted may be used to attach the ATR crystalline layer 68 into the groove 68G. A refractive index of the adhesive agent is smaller than that of the ATR crystalline layer 68.

A method of measuring subject contact pressure by using the pressure measuring apparatus 100 according to an embodiment will now be described with reference to FIGS. 1 and 8.

Figure 8:
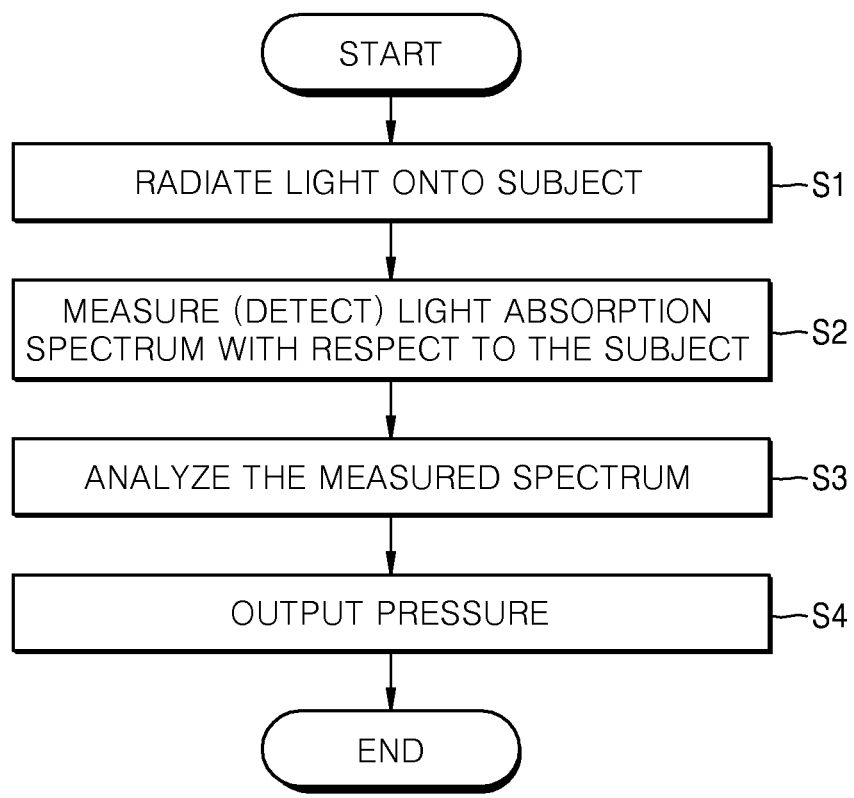
FIG. 8 is a flowchart of a method of measuring a subject contact pressure by using an apparatus for measuring subject contact pressure according to an exemplary embodiment.

As shown in FIG. 8, light is radiated onto the subject 72 (operation S1) through the ATR crystalline layer 68 of the pressure measuring apparatus 100. Light incident onto the ATR crystalline layer 68 with an incident angle between the light incident surface 68S1 of the ATR crystalline layer 68 and the line perpendicular to the light incident surface 68S1 is reflected from an upper surface of the ATR crystalline layer 68 and a part of the light is absorbed by the subject 72. In this regard, degree of light absorption of the subject 72 may differ according to contact pressure of the subject 72 contacting the ATR crystalline layer 68.

Thereafter, a light absorption spectrum with respect to the subject 72 is measured (detected) (operation S2). In more detail, the light incident onto the ATR crystalline layer 68 is repeatedly reflected from upper and lower surfaces of the ATR crystalline layer 68 and is emitted through the light emission surface 68S2 of the ATR crystalline layer 68. During the process, part of the light incident on the upper surface of the ATR crystalline layer 68 is absorbed by the subject 72. Thus, the light emitted through the light emission surface 68S2 of the ATR crystalline layer 68 includes light absorption information of the subject 72. The light emitted through the light emission surface 68S2 of the ATR crystalline layer 68 is incident onto and detected by the spectrum analyzer 64. The spectrum analyzer 64 analyzes a spectrum of the detected light (operation S3). Light intensity data of a predetermined location of the spectrum of the detected light may be determined by the spectrum analysis. Contact pressure is output by the light intensity data obtained through the spectrum analysis (operation S4). The contact pressure may be output by using a program that uses a light intensity-contact pressure database. The output contact pressure may be a contact pressure of the subject 72.

The subject 72 provided in the pressure measuring apparatus and the manufacturing and measuring methods described above may be, for example, the skin of a living body, a finger, a toe, etc. but is not limited thereto.

An apparatus for measuring subject contact pressure, according to at least one embodiment, measures the subject contact pressure by using a change in light absorption of a subject. Thus, a configuration of the apparatus may be simpler than that of an existing mechanical apparatus, and the reliability of measured data may be increased.

What is claimed is:

1. An apparatus for measuring a contact pressure, the apparatus comprising:
   a first material layer configured to provide a light path along which incident light travels to a subject being in contact with the first material layer;
   a spectrum analyzer configured to detect light emitted from the first material layer and perform a light absorption spectrum analysis on the detected light based on a wavelength or a range of wavelengths of the detected light to determine an intensity of the detected light;
   a pressure calculator configured to determine a contact pressure of the subject based on the determined intensity based on the wavelength or the range of wavelengths of the detected light; and
   a second material layer configured to embed the entire structure of the spectrum analyzer,
   wherein the light emitted from the first material layer is incident on the spectrum analyzer through the second material layer.

2. The apparatus of claim 1, further comprising a substrate on which the spectrum analyzer and the pressure calculator are mounted.

3. The apparatus of claim 1, wherein the pressure calculator is separately and independently provided from the first material layer and the spectrum analyzer.

4. The apparatus of claim 3, further comprising a substrate on which the spectrum analyzer is mounted,
   wherein the pressure calculator is provided outside the substrate, and the pressure calculator is electrically connected to the spectrum analyzer through the substrate.

5. The apparatus of claim 3, further comprising:
   a substrate on which the spectrum analyzer is mounted,
   a contact pad provided on the substrate, wherein the pressure calculator is electrically connected to the spectrum analyzer through the contact pad.

6. The apparatus of claim 1, wherein the spectrum analyzer comprises light absorption spectrum data measured at various contact pressures.

7. The apparatus of claim 1, wherein the pressure calculator comprises mapping data indicating relation between a plurality of contact pressure values and a corresponding plurality of light intensity values.

8. The apparatus of claim 1, wherein the first material layer is an attenuated total reflectance crystalline layer.

9. The apparatus of claim 1, further comprising a light source configured to emit the incident light to the first material layer with an incidence angle and adjust the incidence angle to be greater than a critical angle to occur total internal reflection.

10. A method of manufacturing a contact pressure measuring apparatus, the method comprising:
    providing a light source and a spectrum analyzer on a substrate, the spectrum analyzer being configured to perform light absorption spectrum analysis based on a wavelength or a range of wavelengths of a detected light from the light source;
    forming, on the substrate, a structure that covers the light source and the spectrum analyzer;
    forming a first material layer which is disposed on a surface of the structure and has a total reflection characteristic; and
    providing a pressure calculator connected to the spectrum analyzer, the pressure calculator being configured to determine a contact pressure based on the wavelength or the range of wavelengths of the detected light,
    wherein light emitted from the first material layer is incident on the spectrum analyzer through the structure, and
    wherein the structure is a second material, which embeds the entire structure of the spectrum analyzer.

11. The method of claim 10, wherein the pressure calculator is provided on the substrate.

12. The method of claim 10, wherein the pressure calculator is provided outside the substrate.

13. The method of claim 10, wherein
    the method further comprises:
    forming a groove on the second material layer to mount the first material layer thereon; and
    attaching the first material layer onto the groove.

14. The method of claim 10, wherein the first material layer is an attenuated total reflectance crystalline layer.

15. A method of measuring subject contact pressure, the method comprising:
    detecting a light emitted from a first material layer provided in a light path along which incident light travels to a subject being in contact with the first material layer;
    analyzing the detected light by performing a light absorption spectrum analysis, by a spectrum analyzer, on the detected light based on a wavelength or a range of wavelengths of the detected light;
    obtaining light intensity data based on a result of the analyzing; and
    outputting a pressure value corresponding to the obtained light intensity data based on the wavelength or the range of wavelengths of the detected light,
    wherein the entire structure of the spectrum analyzer is embedded in a second material layer, and
    wherein the light emitted from the first material layer is incident on the spectrum analyzer through the second material layer.

16. The method of claim 15, wherein the detecting the light comprises:
    radiating light into the first material layer; and
    detecting the light emitted through a light emission surface of the first material layer.

17. The method of claim 15, further comprising displaying the output pressure value on a display.

* * * * *